United States Patent
Fujii et al.

(10) Patent No.: US 9,295,261 B2
(45) Date of Patent: Mar. 29, 2016

(54) AQUEOUS MICROEMULSIONS CONTAINING PYRETHROID COMPOUNDS

(75) Inventors: Shingo Fujii, Toyohashi (JP); Munehiro Suzuki, Toyohashi (JP); Osamu Yamada, Toyohashi (JP)

(73) Assignee: AGRO-KANESHO CO. LTD., Tokyo (JP)

( * ) Notice: Subject to any disclaimer, the term of this patent is extended or adjusted under 35 U.S.C. 154(b) by 1060 days.

(21) Appl. No.: 12/282,529

(22) PCT Filed: Mar. 28, 2007

(86) PCT No.: PCT/EP2007/052972
§ 371 (c)(1),
(2), (4) Date: Sep. 23, 2008

(87) PCT Pub. No.: WO2007/110435
PCT Pub. Date: Oct. 4, 2007

(65) Prior Publication Data
US 2010/0292323 A1 Nov. 18, 2010

(30) Foreign Application Priority Data
Mar. 29, 2006 (EP) .................................... 06006601

(51) Int. Cl.
*A01N 53/00* (2006.01)
(52) U.S. Cl.
CPC ...................................... *A01N 53/00* (2013.01)
(58) Field of Classification Search
CPC ...................................................... A01N 53/00
See application file for complete search history.

(56) References Cited

U.S. PATENT DOCUMENTS

| | | | |
|---|---|---|---|
| 5,028,623 A | 7/1991 | Matsunaga et al. | |
| 5,286,749 A | 2/1994 | Kieran et al. | |
| 5,317,042 A | 5/1994 | Narayanan | |
| 5,334,585 A | 8/1994 | Derian et al. | |
| 5,612,047 A * | 3/1997 | Duffy et al. | 424/405 |
| 6,878,674 B2 * | 4/2005 | Kobayashi | 504/136 |

FOREIGN PATENT DOCUMENTS

| | | |
|---|---|---|
| EP | 0432062 | 6/1991 |
| EP | 0500401 | 8/1992 |
| EP | 0645964 | 4/1995 |
| GB | 2110092 | 6/1983 |
| JP | 55076176 A * | 6/1980 |
| JP | 02104508 A * | 4/1990 |
| JP | 3299812 | 7/2002 |
| WO | WO 88/07326 | 10/1988 |
| WO | WO 90/03112 | 4/1990 |
| WO | WO 98/00010 | 1/1998 |
| WO | WO 99/65300 | 12/1999 |

OTHER PUBLICATIONS

International Search Report for International Application No. PCT/EP2007/052972; International Filing Date: Mar. 28, 2007; Date of Completion: May 7, 2008; Date of Mailing: May 15, 2008.
International Preliminary Report on Patentability for International Application No. PCT/EP2007/052972; International Filing Date: Mar. 28, 2007; Date of Submission: Aug. 13, 2008; Date of Completion: Sep. 19, 2008.
Database WPI Week 199021 Derwent Publications Ltd., London, GB; AN 1990-161316 XP002421340 & JP 02 104508 A (Sumitomo Chem Ind KK) Apr. 17, 1990, Search Report.
Database WPI Week 198049 Derwent Publications Ltd., London, GB; AN 1980-87350C XP 002421339 & JP 55 136201 A (Hokko Chem Ind Co LTD) Oct. 23, 1980, Search Report.

* cited by examiner

*Primary Examiner* — Abigail Fisher
*Assistant Examiner* — Daniel L Branson
(74) *Attorney, Agent, or Firm* — Oblon, McClelland, Maier & Neustadt, L.L.P.

(57) ABSTRACT

The present invention relates to new aqueous microemulsions containing organic pesticide compounds of limited water-solubility and to their use for plant protection, including seed and crop protection, and protection or non-living material. The aqueous microemulsions comprise a) at least one pyrethroid compound P; b) at least one organic solvent, selected from compounds of the formula I $R^1$—(O-Alk)$_m$-O—C(O)$R^2$ (I) wherein m is 1, 2 or 3, $R^1$ is H, $C_1$-$C_6$-alkyl or C(O)$R^3$, $R^2$ is hydrogen or $C_1$-$C_4$-alkyl, which may be unsubstituted or substituted with OH, Alk is $C_2$-$C_6$-alkylene, and $R^3$ is hydrogen or $C_1$-$C_4$-alkyl, which may be unsubstituted or substituted with OH; c) at least one surfactant; and d) water.

13 Claims, No Drawings

AQUEOUS MICROEMULSIONS CONTAINING PYRETHROID COMPOUNDS

This application is a National Stage application of International Application No. PCT/EP2007/052972 filed Mar. 28, 2007, the entire contents of which is hereby incorporated herein by reference. This application also claims the benefit under 35 U.S.C. §119 of European Patent Application No. 06006601.6, filed Mar. 29, 2006, the entire contents of which is hereby incorporated herein by reference.

The present invention relates to new aqueous microemulsions containing one or more pyrethroid compounds and to their use for plant protection, including seed and crop protection, and protection or non-living material.

BACKGROUND OF THE INVENTION

Pesticide compound are often applied in the form of a dilute aqueous composition in order to achieve a good interaction with the target organisms, such as plants, fungi and insects. However, most active ingredients that are used as pesticides, in particular pyrethroid compounds, are only sparingly or even insoluble in water, i.e. they usually have a water-solubility of not more than 5 g/l, often not more than 1 g/l and particularly not more than 0.1 g/l at 25° C./1013 mbar. Therefore, formulators are often confronted with difficulties in formulating pesticide compounds in stable formulations that can be easily diluted with water.

Pesticides having a limited solubility in water are often formulated as aqueous suspension concentrate (SC) which can be diluted with water for use in the field. Suspension concentrates are formulations, wherein the active ingredient is present in the form of finely divided solid particles, which are suspended in an aqueous dispersing medium utilizing surface-active compounds (surfactants), such as wetting agents, dispersants and rheological or suspending aids for stabilising the active ingredient particles in the dispersing medium. However, problems are often encountered with SC's as a result of settling during prolonged storage or storage at elevated temperatures, the resistance of settled particles to re-suspension and the formation of crystalline material upon storage. As a consequence, the formulations are difficult to handle and the bioefficacy may be inconsistent. Moreover, SC's are limited to actives that have a relatively high melting point. SC's are often not suitable for the formulating pyrethroid compounds.

An alternative for formulating active ingredients that are sparingly water-soluble are so-called emulsifiable concentrates (EC). In an EC the active ingredient is dissolved in a water-immiscible solvent (solubility usually <0.1 g/l), such as a hydrocarbon solvent, in particular an aromatic hydrocarbon, together with surfactants. EC's are usually stable solutions that can be diluted with water to form a milky oil-in-water (o/w) emulsion, containing the active ingredient in the droplets of the disperse phase. EC formulations have a considerable drawback in that they usually contain considerable amounts of hydrocarbon organic solvents which are not entirely satisfactory with regard to their ecological and toxicological properties. Since the droplets of the o/w emulsion that forms upon dilution with water, the bioefficacy of the active ingredient is sometimes not satisfactory. Moreover, separation of active ingredient may occur upon dilution with water, which may lead to inaccurate dosage and uneven bioefficacy.

Some of the deficiencies of EC-formulations can be overcome by microemulsion (ME) formulation technique. Microemulsions like conventional emulsions, also referred to as macro emulsions, are multiphase systems comprising a disperse phase and a continuous phase. In contrast to macro emulsions, the average particle (droplets) size (Z-average diameter as determined by light scattering) of the disperse phase in microemulsions is at least 5 times smaller than in macro emulsions and generally does not exceed 200 nm, while the average diameter of the droplets in macro emulsions is in μm range. Due to the small particle size (droplet size) of the disperse phase, microemulsions have a translucent appearance.

ME formulation of pesticide compounds are usually water based and additionally contain at least one surfactant and at least one cosolvent or cosurfactant, which is usually an organic solvent or a low molecular weight polyalkylene ether. By using ME formulations risks such as inflammability and toxicity, environmental concerns and costs can are reduced in comparison with EC techniques, because water is the main constituent. Due to the small particle size of the disperse phase containing the active ingredient, an increase in bioavailability can often be achieved. However, it is difficult to maintain the stability of ME formulation of active ingredients having a low water-solubility with respect to the droplet size and uniformity and crystallization of active ingredient may occur. Moreover, it is also difficult to maintain the droplet size stability when the ME formulation is diluted with water. This originates from low solubility of the active ingredient in water. However, a stable droplet size after dilution, i.e. maintaining a small droplet size, is important to achieve preferable biological activities. Therefore, much efforts were made in order to develop the stable water-based microemulsion formulation.

WO 88/07326 and WO 90/03112 describe microemulsions containing an insecticidal compound. The formulations contain a considerable amount of hydrocarbon solvent, surfactant and, as a cosurfactant, low molecular (ethylene oxide/propylene oxide) block copolymers of low HLB.

JP 3299812 describes herbicidal ME formulation which contain aromatic solvents and optionally ketones such cyclohexanone and ester of fatty acids such as methyl oleate as cosolvent.

WO 98/00010 discloses a microemulsion of insecticide compounds containing a hydrocarbon solvent and a cosolvent selected from $C_3$-$C_{12}$ alkanols and etheralkanols such as diethylene glycol monohexyl ether, diethylene glycol monobutyl ether and propylene glycol monobutyl ether.

U.S. Pat. No. 5,317,042 describes an aqueous ME of a pyrethroid insecticide, which contains a $C_1$-$C_4$-alkylpyrrolidone as a cosolvent.

By using lipophilic hydrocarbon solvents such as toluene, xylene or hydrocarbon mixtures such as Solvesso, Exxsol, Shellsol, etc., stable formulation could be obtained, which show reduced tendency of the active ingredient to crystallize. However, these solvents lead to increased skin sensitization. Replacing these solvents by less toxic polar solvents such as N-alkypyrrolidones, $C_1$-$C_3$-alkanols, ketones, ethylene glycol, propylene glycol, di-$C_2$-$C_3$-alkylene glycols etc. leads to reduced stability of the dilution originating from reduced solubility of active ingredient in the solvent under the diluted conditions. The aforementioned problems are particularly pronounced in case of pyrethroid compounds.

Therefore, there is an ongoing need for ME formulations of pyrethroid compounds which are uniform and stable. In particular, the formulation should be stable upon dilution with water, i.e. they should provide stable size distribution of small droplets after dilution with water. Moreover, they should provide reduced tendency of the active ingredient to crystallize, in particular after dilution of the formulation with water.

Moreover the ME formulation should maintain its liquid state at low temperatures, i.e. at temperature below 0° C. It is highly desirable to achieve these objects without the use of hydrocarbon solvent, in order to increase ecological compatibility and to reduce the risk of skin irritation. In particular ME formulations are required which provide stable formulations of pyrethroid esters, in particular pyrethroid esters having a biphenylether moiety and especially flucythrinate or alpha cypermethrin or mixtures thereof.

SUMMARY OF THE INVENTION

This object could surprisingly be solved by providing a microemulsion formulation that contains an organic solvent of the formula I as defined herein and a surfactant mixture comprising at least one anionic surfactant and at least one non-ionic surfactant.

Therefore, the present invention relates to a formulation of pyrethroid compounds P in the form of an aqueous microemulsion, the formulation comprising
a) at least pyrethroid compound P;
b) at least one organic solvent, selected from compounds of the formula I

wherein m is 1, 2 or 3,
$R^1$ is H, $C_1$-$C_6$-alkyl or $C(O)R^3$,
$R^2$ is hydrogen or $C_1$-$C_4$-alkyl, which may be unsubstituted or substituted with OH,
Alk is straight chain or branched $C_2$-$C_6$-alkylene, and
$R^3$ is hydrogen or $C_1$-$C_4$-alkyl, which may be unsubstituted or substituted with OH;
c) a surfactant mixture comprising;
   c.1 at least one anionic surfactant and
   c.2 at least one non-ionic surfactant; and
d) water.

The microemulsions of the invention are stable liquid formulations that are clear and stable against formation of solids upon storage. Moreover they remain liquid at temperatures below 0° C., without losing their beneficial properties. Their freezing point is usually below –5° C.

The ME formulations of the invention can be easily diluted with water without the formation of coarse material and the aqueous dilutions have enhanced physical stability, i.e. the formation of solids after dilution is not observed even after storage for a prolonged period of time, e.g. after 24 h at room temperature no crystallization is observed. Upon dilution with water, the compositions of the present invention form a bluish or even clear emulsion, indicating that the droplets/particles dispersed therein are of very small size. The average particle diameter of the droplets/particles will usually not exceed 200 nm, in particular 100 nm, more particularly 50 nm and may be 10 nm or even less than 10 nm. The small particle/size is maintained even after storage for a prolonged period of time, e.g. after storage for 24 h at room temperature the increase in particle size is generally less than 10%. The average particle size as referred herein, are Z average particle diameters which can be determined by dynamic light scattering. A skilled person is familiar with these methods which are e.g. described in H. Wiese (D. Distler, Ed.), Aqueous Polymer Dispersions (Wässrige Polymerdispersionen), Wiley-VCH 1999, Chapter 4.2.1, p. 40ff, and the literature cited therein; H. Auweter, D. Horn, J. Colloid Interf. Sci. 105 (1985), p. 399; D. Lilge, D. Horn, Colloid Polym. Sci. 269 (1991), p. 704; and H. Wiese, D. Horn, J. Chem. Phys. 94 (1991), p. 6429. Due to the small particle size after dilution with water the bioavailability and thus the biological activity of the active ingredient is often increased, in comparison with conventional formulations. Moreover no hydrocarbon solvents are required to achieve the beneficial properties of the microemulsions of the invention. Thus, the ecological compatibility of the formulations is superior and the risk of skin irritation can be reduced.

The microemulsions of the present invention will usually be an oil-in-water emulsion, i.e. water forms the continuous phase, while solvent and pyrethroid compound P is present in the disperse phase. They can be obtained for example by simply mixing the ingredients, by mixing a preformed solution of the pyrethroid compound P in the solvent of formula II either by adding water to the solution or by adding the solution to water.

In particular ME formulations according to the present invention provide stable formulations of pyrethroid compounds in particular pyrethroid esters, more preferably pyrethroid esters having a biphenylether moiety and especially flucythrinate or alpha cypermethrin or mixtures thereof.

DETAILED DESCRIPTION OF THE INVENTION

As used herein the term alkyl refers to saturated straight-chain or branched hydrocarbon radicals having the numbers of carbon atoms given in the prefix. Thus, $C_1$-$C_6$-alkyl refers to saturated straight-chain or branched hydrocarbon radicals having 1 to 4, 5 or 6-carbon atoms, especially 1 to 4 carbon atoms ($C_1$-$C_4$-alkyl) such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

As used herein the term $C_2$-$C_6$-alkylene refers to a saturated, divalent straight chain or branched hydrocarbon chains of 2, 3, 4, 5 or 6 carbon groups, examples including ethane-1,2-diyl, propane-1,3-diyl, propane-1,2-diyl, 2-methylpropane-1,2-diyl, 2,2-dimethylpropane-1,3-diyl, butane-1,4-diyl, butane-1,3-diyl (=1-methylpropane-1,3-diyl), butane-1,2-diyl, butane-2,3-diyl, 2-methyl-butan-1,3-diyl, 3-methyl-butan-1,3-diyl (=1,1-dimethylpropane-1,3-diyl), pentane-1,4-diyl, pentane-1,5-diyl, pentane-2,5-diyl, 2-methylpentane-2,5-diyl (=1,1-dimethylbutane-1,3-diyl) and hexane-1,6-diyl.

As used herein, the term aryl refers to phenyl or naphthyl.

The microemulsions of the invention contain at least one solvent of the formula I as described above. Amongst the solvents of the formula I those are preferred, wherein the variables, independently of each other, preferably in combination, have the meanings given below:
m is 1 or 2, in particular 1,
$R^1$ is $C_1$-$C_6$-alkyl or $C(O)R^3$, in particular methyl or ethyl,
$R^2$ is $C_1$-$C_4$-alkyl, in particular methyl,
Alk is $C_3$-$C_6$-alkylene, in particular propan-1,3-diyl, butan-1,3-diyl, butan-1,4-diyl, and 3-methyl-butan-1,3-diyl, or
Alk may also be ethan-1,2-diyl if $R^1$ is $C_3$-$C_6$-alkyl or $C(O)R^3$, and
$R^3$ is $C_1$-$C_4$-alkyl, in particular methyl.

Examples of preferred solvents include 3-methoxy-3-methyl butyl acetate, propylene glycol mono methyl ether acetate, propylene glycol mono ethyl ether acetate, dipropylene glycol methyl ether acetate, propylene glycol diacetate, ethylene glycol mono butyl ether acetate, diethylene glycol mono butyl ether acetate, and mixtures thereof. Particular preference is given to 3-methoxy-3-methyl butyl acetate, propylene glycol mono methyl ether acetate and propylene glycol mono ethyl ether acetate.

The amount of solvent in the microemulsion formulation according to the invention generally depends on the amount of pyrethroid compound P. In general, the weight ratio of organic solvent of formula I to the pyrethroid compound P is from 0.5:1 to 100:1, preferably from 1:1 to 50:1, in particular from 1.5:1 to 30:1. The total amount of solvent will be generally in the range of 0.1 to 30% by weight, in particular from 1 to 25% by weight and more preferably from 5 to 20% by weight, based on the total weight of the formulation.

The microemulsion formulation of the present invention also contains a surfactant mixture comprising at least one anionic surfactant and at least one non-ionic surfactant. The term "surfactant" denotes surface active compounds, which, below, are also termed as detergent or emulsifier. The surfactant mixture serves to reduce surface tension between the continuous and the disperse phase, thereby stabilizing the droplets of the disperse phase. The surfactant also assists in the solubilisation of the pyrethroid compound P. Suitable surfactants for microemulsion formulations are well known in the art, e.g. from McCutcheon's Detergents and Emulsifiers, Int. Ed., Ridgewood, N.Y. The surfactants may be polymeric surfactants or non-polymeric surfactants. Preferably, the major amount, preferably at least 90%, in particular the total amount of surfactant present in the microemulsion is selected from non-polymeric surfactants, also termed emulsifier. Non-polymeric surfactants (emulsifiers), in contrast to polymeric surfactants, will generally have a molecular weight of below 2000 Dalton (number average), in particular from 150 to 2000 Dalton, preferably from 200 to 1500 Dalton.

Anionic surfactants include in particular the sodium, potassium, calcium or ammonium salts of
- $C_6$-$C_{22}$-alkylsulfonates such as lauryl sulfonate, isotridecylsulfonate;
- $C_6$-$C_{22}$-alkylsulfates such as lauryl sulfate, isotridecylsulfate, cetylsulfate and stearylsulfate;
- aryl- and sulfonates, in particular $C_1$-$C_{16}$-alkylbenzene sulfonates, such as cumylsulfonate, octylbenzene sulfonate, nonylbenzene sulfonate, and dodecylbenzene sulfonate, naphtholsulfonate, mono- and di-$C_1$-$C_{16}$-alkylnaphthyl sulfonates such as dibutylnaphthylsulfonate;
- mono- and di-$C_1$-$C_{16}$-alkyldiphenylether (di)sulfonates such as dodecyldiphenylether disulfonate;
- sulfates and sulfonates of fatty acids and fatty acid esters;
- polyoxy-$C_2$-$C_3$-alkylene $C_8$-$C_{22}$-alkyl ether sulfates, in particular sulfates of ethoxylated $C_8$-$C_{22}$ alkanols such as sulfates of ethoxylated lauryl alcohol;
- polyoxy-$C_2$-$C_3$-alkylene $C_1$-$C_6$-alkylbenzene ether sulfates, in particular sulfates of ethoxylated $C_1$-$C_{16}$-alkylphenols;
- di $C_4$-$C_{18}$ alkylesters of sulfosuccinic acid (=$C_4$-$C_{18}$-dialkyl sulfosuccinates) such as dioctylsulfosuccinate;
- condensates of naphthalenesulfonic acid, $C_1$-$C_{16}$-alkyl naphthalenesulfonic acid or phenolsulfonic acid with formaldehyde (=($C_1$-$C_{16}$-alkyl) naphthalene sulfonate-formaldehyde condensates and phenolsulfonate formaldehyde condensates);
- polyoxy-$C_2$-$C_3$-alkylene mono- di- or tristyryl phenyl ether sulfates, in particular polyethoxylates of mono-, di- or tristyrylphenol;
- mono- and di-$C_8$-$C_{22}$-alkyl sulfates;
- polyoxy-$C_2$-$C_3$-alkylene $C_8$-$C_{22}$-alkyl ether phosphates;
- polyoxy-$C_2$-$C_3$-alkylene $C_1$-$C_6$-alkylbenzene ether phosphates;
- polyoxy-$C_2$-$C_3$-alkylene mono- di- or tristyryl phenyl etherphosphates;
- polyoxyethylene polycarboxylates, in particular homo- and copolymers of monoethylenically unsaturated mono- or dicarboxylic acids having from 3 to 8 carbon atoms, the copolymers also having polyethylene oxide side chains;
- salts of fatty acids such as stearates; and
- polyphosphates such as hexametaphosphates and triphosphates (=tripolyphosphate).

Non-ionic surfactants include in particular
- polyoxy-$C_2$-$C_3$-alkylene $C_8$-$C_{22}$-alkyl ethers, in particular polyethoxylates and poly-ethoxylates-co-propoxylates of linear or branched $C_8$-$C_{22}$-alkanols, more preferably polyethoxylated fatty alcohols and polyethoxylated oxoalcohols, such as polyethoxylated lauryl alcohol, polyethoxylated isotridecanol, polyethoxylated cetyl alcohol, polyethoxylated stearyl alcohol, and esters thereof, such as acetates;
- polyoxy-$C_2$-$C_3$-alkylene aryl ethers and polyoxy-$C_2$-$C_3$-alkylene $C_1$-$C_{16}$-alkylaryl ethers, such as polyoxy-$C_2$-$C_3$-alkylene $C_8$-$C_{22}$-alkylbenzene ethers, in particular polyethoxylates of $C_1$-$C_{16}$-alkylphenoles, such as polyethoxylates of nonylphenol, decylphenol, isodecylphenol, dodecylphenol or isotridecylphenol,
- polyoxy-$C_2$-$C_3$-alkylene mono-, di- or tristyryl phenyl ethers, in particular polyethoxylates of mono-, di- and tristyrylphenoles; and the formaldehyde condensates thereof and the esters thereof, e.g. the acetates;
- $C_6$-$C_{22}$-alkylglucosides and $C_6$-$C_{22}$-alkyl polyglucosides;
- polyethoxylates of $C_6$-$C_{22}$-alkylglucosides and polyethoxylates of $C_6$-$C_{22}$-alkyl polyglucosides;
- polyethoxylates of fatty amines;
- polyethoxylates of fatty acids and polyethoxylates of hydroxyl fatty acids;
- partial esters of polyols with $C_6$-$C_{22}$-alkanoic acids, in particular mono- and diesters of glycerine and mono-, di- and triesters of sorbitan, such as glycerine monostearate, sorbitanmonooleat, sorbitantristearat;
- polyethoxylates of partial esters of polyols with $C_6$-$C_{22}$-alkanoic acids, in particular polyethoxylates of mono- and diesters of glycerine and polyethoxylates of mono-, di- and triesters of sorbitan, such as polyethoxylates of glycerine monostearate, polyethoxylates of sorbitanmonooleat, polyethoxylates of sorbitanmonostearat and polyethoxylates of sorbitantristearat;
- polyethoxylates of vegetable oils or animal fats such as corn oil ethoxylate, castor oil ethoxylate, tallow oil ethoxylate;
- acetylene glycols such as 2,4,7,9-tetramethyl-4,7-bis(hydroxy)-5-decyne;
- polyoxyethylene-polyoxypropylene-blockcopolymers; and
- polyethoxylates of fatty amines, fatty amides or of fatty acid diethanolamides.

The term polyoxy-$C_2$-$C_3$-alkylene ether refers to polyether radicals derived from ethyleneoxide or propyleneoxide. The term polyethoxylate refers to a polyether radical derived from ethyleneoxide. Likewise, the term polyoxyethylene-co-polyoxypropylene refers to a polyether radical derived from a mixture of ethyleneoxide and propyleneoxide. The number of repeating units in the polyether radicals will generally vary from 2 to 100, frequently from 4 to 100 and in particular from 5 to 50.

Preferably, the surfactant, if present, comprises at least 50% by weight, based on the total amount of surfactant present, of the surfactant mixture, comprising at least one non-ionic surfactant and at least one anionic surfactant. In particular, the surfactant mixture amounts to at least 80% by weight, in particular at least 90% by weight, based on the total amount of surfactant present in the formulation. More preferably the surfactant is exclusively selected from the mixture of the at least one anionic surfactant and the at least one non-ionic surfactant.

Preferred anionic surfactants are selected from the aforementioned:
- $C_1$-$C_{16}$-alkyl benzene sulfonates;
- $C_1$-$C_{16}$-alkyl naphthalene sulfonates;
- naphthalene sulfonate-formaldehyde condensates and $C_1$-$C_{16}$-alkyl naphthalene sulfonate-formaldehyde condensates;
- polyoxy-$C_2$-$C_3$-alkylene $C_8$-$C_{22}$-alkyl ether sulfates;
- polyoxy-$C_2$-$C_3$-alkylene $C_8$-$C_{22}$-alkyl ether phosphates;
- polyoxy-$C_2$-$C_3$-alkylene $C_1$-$C_{16}$-alkylbenzene ether sulfates;
- polyoxy-$C_2$-$C_3$-alkylene $C_1$-$C_{16}$-alkylbenzene ether phosphates,
- $C_8$-$C_{22}$-alkyl sulfates,
- $C_4$-$C_8$-dialkyl sulfosuccinates,
- polyoxy-$C_2$-$C_3$-alkylene mono- di- or tristyryl phenyl ether sulfates,
- polyoxy-$C_2$-$C_3$-alkylene mono- di- or tristyryl phenyl etherphosphates,
- polyoxyethylene polycarboxylates and
- polyphosphates, and mixtures thereof.

Particularly preferred anionic surfactants include the salts, in particular the sodium, potassium and calcium salts of $C_8$-$C_{22}$-alkyl sulfates, $C_1$-$C_{16}$-alkyl naphthalene sulfonates, $C_1$-$C_{16}$-alkyl benzene sulfonates, in particular $C_1$-$C_{16}$-alkyl benzene sulfonates.

Preferred non-ionic surfactants are selected from the aforementioned:
- polyoxy-$C_2$-$C_3$-alkylene $C_8$-$C_{22}$-alkyl ethers,
- polyoxy-$C_2$-$C_3$-alkylene $C_8$-$C_{22}$-alkylbenzene ethers,
- polyoxy-$C_2$-$C_3$-alkylene mono-, di- or tristyryl phenyl ethers,
- polyoxy-$C_2$-$C_3$-alkylene mono- or distyryl phenyl ether-formaldehyde condensates,
- acetylene glycols and the mixtures thereof.

Particularly preferred non-ionic surfactants include polyoxy-$C_2$-$C_3$-alkylene mono-, di- or tristyryl phenyl ethers and polyoxy-$C_2$-$C_3$-alkylene mono- or distyryl phenyl ether-formaldehyde condensates, and mixtures thereof.

In a preferred embodiment of the invention, the surfactant present in the microemulsion is selected from a mixture comprising
(i) at least one anionic surfactant, in particular at least one, e.g. one or two, of the preferred anionic surfactants, and
(ii) at least one non-ionic surfactant, in particular at least one, e.g. one, two or three, of the preferred non-ionic surfactants.

In a very preferred embodiment of the invention, the surfactant present in the microemulsion is selected from a mixture comprising
(i) at least one anionic surfactant selected from $C_1$-$C_{16}$-alkyl benzene sulfonates, and
(ii) at least one non-ionic surfactant selected from polyoxy-$C_2$-$C_3$-alkylene mono-, di- or tristyryl phenyl ethers and polyoxy-$C_2$-$C_3$-alkylene mono- or distyryl phenyl ether-formaldehyde condensates.

The weight ratio of anionic and non-ionic surfactant in the surfactant mixture is preferably from 0.1:1 to 10:1 in particular from 2:1 to 1:5.

The amount of surfactant in the microemulsion formulation according to the invention generally depends on the amount of pyrethroid compound P and solvent. The weight ratio of surfactant to the total amount of solvent I plus pyrethroid compound P will usually be in the range from 0.1:1 to 10:1, preferably from 5:1 to 1:5 in particular from 2:1 to 1:2. Usually, the surfactant will be present in an amount ranging from 1 to 30% by weight, based on the total weight of the solution before crystallization, in particular from 5 to 20% by weight, based on the total weight of the microemulsion.

The total amount of solvent and surfactant in the microemulsion formulation according to the invention generally depends on the amount of pyrethroid compound P. In general, the weight ratio of organic solvent of formula I plus surfactant to the pyrethroid compound P is from 200:1 to 1:1, preferably from 100:1 to 1.5:1, in particular from 50:1 to 2:1. The total amount of solvent+surfactant will be generally in the range of 1.1 to 60% by weight, in particular from 6 to 50% by weight and more preferably from 10 to 40% by weight, based on the total weight of the formulation.

The microemulsions of the invention also comprise at least one pyrethroid compound P. In general, the pyrethroid compound is sparingly soluble or insoluble in water. Generally, the solubility is below 5 g/l, mostly below 1 g/l, frequently below 0.5 g/l and in particular below 0.1 g/l at 25° C. and 1013 mbar. Usually, the pyrethroid compound P is soluble in the organic solvent I, i.e. the compound P has a solubility in the solvent of the formula I of at least 10 g/l, more preferably at least 50 g/l and particularly preferably at least 100 g/l at 25° C.

The amount of pyrethroid compound P is usually in the range from 0.0001 to 20% by weight, frequently in the range from 0.01 to 10% by weight, in particular from 0.1 to 8% by weight and more preferably from 0.5 to 5% by weight, based on the total weight of the microemulsion.

The term "pyrethroid compound P" includes natural and synthetic pyrethroids, including pyrethroid ether and pyrethroid esters, and synthetic pyrethroid analogs such as 1,4-diaryl-1-(cyclopropyl or isopropyl)-2-fluoro-2-butenes. Examples of pyrethroid compounds include pyrethroid esters such as acrinathrin, allethrin, barthrin, bifenthrin, bioallethrin, bioethanomethrin, biopermethrin, bioresmethrin, cismethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, esfenvalerate, fenfluthrin, fenpirithrin, fenpropathrin, fenvalerate, flucythrinate, fluvalinate, flurethrin, imiprothrin, metofluthrin, permethrin, phenothrin, prallethrin, profluthrin, pyresmethrin, pyrethrin I and II, resmethrin, taufluvalinate, tefluthrin, terallethrin, tetramethrin, tralomethrin and transfluthrin, pyrethroid ethers such as etofenprox, flufenprox, halfenprox, protrifenbute and silafluofen, and structurally comparable compounds such as 1-[1-(p-chlorophenyl)-2-fluoro-4-(4-fluoro-3-phenoxyphenyl)-2-butenyl]-cyclopropane (R,S)-(Z), and mixtures thereof.

Preferred pyrethroid compounds comprise a biphenylether moiety, wherein the phenyl ring may carry one or more, e.g. 1, 2 or 3 substituent radicals selected from fluorine or methyl. Preferred pyrethroid compounds according to the present invention are pyrethroid esters. These compounds can be described by the general formula P'

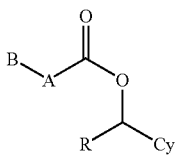

(P')

wherein
A is 2-methylpropan-1,1-diyl, cyclopropan-1,1-diyl, cyclopropan-1,2-diyl which may carry 1, 2 or 3 substituents selected from methyl and chlorine;
B is methyl, 1,2,2,2-tetrabromoethyl, phenyl, which may carry 1 or 2 radicals $R^b$, phenylamino, which may carry 1 or 2 radicals $R^b$, wherein $R^b$ is selected from chlorine fluorine, trifluoromethyl, difluormethoxy, methoxy and ethoxy,
   or B is a radical $CR^x=CR^yR^z$, wherein $R^x$ is hydrogen or halogen, in particular chlorine or bromine, $R^y$, $R^z$ are independently of each other selected from fluorine, chlorine, bromine, methyl, $C_1$-$C_3$-alkoxyoxycarbonyl, such as methoxycarbonyl, ethoxycarbonyl or propoxycarbonyl and $C_1$-$C_3$-haloalkoxycarbonyl, such as difluormethoxycarbonyl, trifluoroethoxycarbonyl, 2,2,2-trifluoroethoxycarbonyl, 1,1,1,3,3,3-hexafluoropropan-2-yl, or $R^y$, $R^z$ together are $C_3$-$C_5$-alkylene, e.g. 1,3-propandiyl, 1,4-butandiyl or 1,5-pentandiyl;
R hydrogen or cyano and
Cy is a cyclic radical selected from phenyl and furyl, which are unsubstituted or which carry a radical selected from methyl, fluorine, methoxymethyl, phenyl, benzyl and phenoxy, and/or 1, 2, 3 or 4 radicals selected from methyl and fluorine and/or 2 radicals, which are bound of adjacent carbon atoms of phenyl form a moiety $OCH_2O$;
   or Cy is imidazolidin-2,5-dion-1-yl, which may carry in the 3-position a radical selected from propen-3-yl and propyn-3-yl, hexahydroisoindol-1,3-dion-2-yl or $C_2$-$C_6$-alkenyl; or
R and Cy together with the carbon atom to which they are bound form a 2,3-cyclopenten-1-on-4-yl radical, which may carry in the 4-position a radical selected from propen-3-yl, propyn-3-yl, 2-furylmethyl.

Preferably Cy is 4-phenoxyphenyl, wherein the phenyl ring may carry a radical selected from methyl, fluorine or chlorine. R is preferably cyano.

In particular, the pyrethroid compound P is the only pesticide compound P in the microemulsion or amounts to at least 90% by weight of the total amount of pesticide compounds in the microemulsion. In a particular preferred embodiment the pyrethroid compound P is selected from alpha cypermethrin and flucythrinate.

The microemulsion of the invention also contains water. The amount of water is at least 40% by weight, in particular at least 50% by weight and more preferably at least 60% by weight. It is self-evident that the amount of water together with the amounts given for the other ingredients adds to 100% by weight.

The microemulsion of the invention may further contain customary auxiliaries, such as defoamers, thickeners, preservatives, colorants, stabilizers, anti-freeze agents and the like which are usually employed in aqueous formulations of pesticides. The total amount of these auxiliaries will usually not exceed 15% by weight, in particular 10% by weight of the microemulsion. The total amount of these auxiliaries, except for anti-freeze agents will usually not exceed 5% by weight, in particular 3% by weight of the microemulsion.

Suitable thickening agents include inorganic thickening agents, such as clays, hydrated magnesium silicates and organic thickening agents, such as polysaccharide gums, like xanthan gum, guar gum, gum arabic and cellulose derivatives. Organic thickening agents are employed in amounts of from 0.5 to 30 g/l and preferably from 1 to 10 g/l while inorganic thickening agents are employed in amounts of from 0.5 to 30 g/l and preferably from 1 to 10 g/l of the microemulsion composition.

Suitable preservatives to prevent microbial spoiling of the compositions of the invention include formaldehyde, alkyl esters of p-hydroxybenzoic acid, sodium benzoate, 2-bromo-2-nitropropane-1,3-diol, o-phenylphenol, thiazolinones, such as benzisothiazolinone, 5-chloro-2-methyl-4-isothiazolinone, pentachlorophenol, 2,4-dichlorobenzyl alcohol and mixtures thereof. In general, the amount of preservatives will be from 0.1 to 10 g/l of the microemulsion composition.

Suitable defoamers include polysiloxanes, such as polydimethyl siloxane. Defoamers are usually employed in amounts of from 0.1 to 5 g/l of the microemulsion composition.

Suitable stabilizers comprise e.g. UV-absorbers such as cinnamic esters, 3,3-diphenyl-2-cyano acrylates, hydroxy and/or alkoxy substituted benzophenones, N-(hydroxyphenyl)-benzotriazoles, hydroxyphenyl-s-triazines, oxalic amides and salicylates, e.g. the UVINUL® 3000, 3008, 3040, 3048, 3049, 3050, 3030, 3035, 3039, 3088, UVINUL® MC80 and radical scavengers, e.g. ascorbic acid, sterically hindered amines (HALS-compounds) such as UVINUL® 4049H, 4050H and 5050H, and the like and anti-oxidants such as vitamin E. In general, the amount of stabilizer will be from 0.01 to 10 g/l of the microemulsion composition.

Suitable anti-freeze agents include $C_1$-$C_4$-alkanols and $C_2$-$C_4$-alkylpolyols such as ethanol, propanol, ethylene glycol, propylene glycol etc. If present, the amount of antifreeze agents will be from 1 to 100 g/l, in particular from 1 to 50 g/l of the microemulsion.

These customary auxiliaries may be contained within the composition of the present invention. However, it is also possible to add these auxiliaries after dilution with water to the ready-to-use aqueous composition.

The microemulsions of the present invention can be simply prepared by mixing the ingredients until an apparently homogeneous liquid has been formed. The sequence of the addition of the ingredients is of minor importance. For example the ingredients can be given into a vessel and the thus obtained mixture is homogenized, e.g. by stirring, until an apparently homogeneous liquid has been formed. However it is also possible to dissolve the pyrethroid compound P in the organic solvent of formula I or in the mixture of said solvent and surfactant and to mix the thus obtained solution with water and the remaining ingredients, e.g. by adding the solution to water or by addition of water to the solution. The temperature of mixing and the mixing conditions are of minor importance. Usually the ingredients are mixed at a temperature ranging from 10 to 90° C., in particular from 10 to 60° C. Higher temperatures, e.g. 35° C. or 40° C. or higher might be useful to expedite the formation of the microemulsion. However, mixing can also be achieved at lower temperatures e.g. from 10° C. to 35° C. or 40° C.

Depending on the type of pyrethroid compound P, the microemulsions of the invention are useful for combating a large number of harmful pests both in plant cultures and seeds but also in non-living material and in household.

The term "pests" as used herein relates to all types of pests which can be combated or controlled by pyrethroid compounds, including insect pest and arachnid pest.

Therefore the present invention also relates to the use of the microemulsions described herein for combating harmful pests; and a method of combating harmful organisms, which comprises contacting said harmful organisms, their habit, breeding ground, food supply, plant, seed, soil, area, material or environment in which the harmful organisms are growing or may grow, or the materials, plants, seeds, soils, surfaces or spaces to be protected from attack or infestation by harmful organisms with an effective amount of the microemulsions described herein.

In a first aspect of the invention the microemulsions described herein are used for plant protection, including treatment of seeds, in particular to the use for protecting crops from attack or infestation by harmful pests, i.e. for combating animal organisms that are harmful to plants or for protecting crops from attack or infestation by such a harmful organism. The present invention particularly relates to the use of the microemulsion for plant protection and in particular to a method of combating pests that are harmful to plants such as insects, arachnids or nematodes, in particular insects and arachnids, which method comprises contacting said harmful organisms, their habit, breeding ground, food supply, plant, seed, soil, area, material or environment in which the harmful organisms are growing or may grow, or the materials, plants, seeds, soils, surfaces or spaces to be protected from attack or infestation by harmful organisms with an effective amount of an aqueous microemulsions as described herein. The invention also relates to a method for protecting crops from attack or infestation by harmful organisms such as weeds, fungi, insects, arachnids or nematodes, which comprises contacting a crop with an effective amount of an aqueous microemulsions as described herein.

In most instances, the microemulsions are diluted with water before being applied to the locus to be treated. The microemulsions of the invention are usually diluted with at least 1 part of water, preferably at least 10 parts of water, in particular at least 100 parts of water, e.g. with 1 to 10,000, in particular from 100 to 5,000 and more preferably with 500 to 2,000 parts of water per one part of the microemulsions (all parts are given in parts by weight).

Dilution will be usually achieved by pouring the microemulsions of the invention into water. Usually, dilution is achieved with agitation, e.g. with stirring, to ensure a rapid mixing of the concentrate in water. However, agitation is not necessary. Though the temperature of mixing is not critical, mixing is usually performed at temperatures ranging from 0 to 50° C., in particular from 10 to 30° C. or at ambient temperature.

The water used for mixing is usually tap water. However the water may already contain water soluble compounds which are used in plant protection, e.g. nutrificants, fertilizers or water soluble pesticides.

The microemulsions of the invention after dilution are applied by usual means which are familiar to a skilled person.

The microemulsions of the present invention may e.g. be applied against the following pests:

Insect pests of the orders:

millipedes (Diplopoda) such as *Blaniulus* species

Ants (Hymenoptera), such as *Atta capiguara, Atta cephalotes, Atta laevigata, Atta robusta, Atta sexdens, Atta texana, Monomorium pharaonis, Solenopsis geminata, Solenopsis invicta, Pogonomyrmex* species and *Pheidole megacephala*, Beetles (Coleoptera), such as *Agrilus sinuatus, Agriotes lineatus, Agriotes obscurus* and other *Agriotes* species, *Amphimallus solstitialis, Anisandrus dispar, Anthonomus grandis, Anthonomus pomorum, Aracanthus morei, Atomaria linearis, Blapstinus* species, *Blastophagus piniperda, Blitophaga undata, Bothynoderes punciventris, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus* and other *Conoderus* species, *Conorhynchus mendicus, Crioceris asparagi, Cylindrocopturus adspersus, Diabrotica* (longicornis) *barberi, Diabrotica semi-punctata, Diabrotica speciosa, Diabrotica undecimpunctata, Diabrotica virgifera* and other *Diabrotica* species, *Eleodes* species, *Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus* and other *Limonius* species, *Lissorhoptrus oryzophilus, Listronotus bonariensis, Melanotus communis* and other *Melanotus* species, *Meligethes aeneus, Melolontha hippocastani, Melolontha melolontha, Oulema oryzae, Ortiorrhynchus sulcatus, Oryzophagus oryzae, Otiorrhynchus ovatus, Oulema oryzae, Phaedon cochleariae, Phyllotreta chrysocephala, Phyllophaga cuyabana* and other *Phyllophaga* species, *Phyllopertha horticola, Phyllotreta nemorum, Phyllotreta striolata,* and other *Phyllotreta* species, *Popillia japonica, Promecops carinicollis, Premnotrypes voraz, Psylliodes* species, *Sitona lineatus, Sitophilus granaria, Sternechus pinguis, Sternechus subsignatus*, and *Tanymechus palliatus* and other *Tanymechus* species, Flies (Diptera) such as *Agromyza oryzea, Chrysomya bezziana, Chrysomya hominivorax, Chrysomya macellaria, Contarinia sorghicola, Cordylobia anthropophaga, Dacus cucurbitae, Dacus oleae, Dasineura brassicae, Delia antique, Delia coarctata, Delia platura, Delia radicum, Fannia canicularis, Gasterophilus intestinalis, Geomyza Tripunctata, Glossina morsitans, Haematobia irritans, Haplodiplosis equestris, Hypoderma lineata, Liriomyza sativae, Liriomyza trifolii, Lucilia caprina, Lucilia cuprina, Lucilia sericata, Lycoria pectoralis, Mayetiola destructor, Muscina stabulans, Oestrus ovis, Opomyza florum, Oscinella frit, Pegomya hysocyami, Phorbia antiqua, Phorbia brassicae, Phorbia coarctata, Progonya leyoscianii, Psila rosae, Rhagoletis cerasi, Rhagoletis pomonella, Tabanus bovinus, Tetanops myopaeformis, Tipula oleracea* and *Tipula paludosa,*

Heteropterans (Heteroptera), such as *Acrosternum hilare, Blissus leucopterus*, Cicadellidae such as *Empoasca fabae,* Chrysomelidae, *Cyrtopeltis notatus,* Delpahcidae, *Dysdercus cingulatus, Dysdercus intermedius, Eurygaster integriceps, Euschistus impictiventris, Leptoglossus phyllopus, Lygus lineolaris, Lygus pratensis, Nephotettix* species, *Nezara viridula,* Pentatomidae, *Piesma quadrata, Solubea insularis* and *Thyanta perditor,*

Aphids and other homopterans (Homoptera), e.g. *Acyrthosiphon onobrychis, Adelges lacis, Aphidula nasturtii, Aphis fabae, Aphis forbesi, Aphis glycines, Aphis gossypii, Aphis grossulariae, Aphis pomi, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes (Myzus) persicae, Myzus ascalonicus, Myzus cerasi, Myzus varians, Nasonovia ribis-nigri, Nilaparvata lugens, Pemphigus bursarius, Pemphigus popu-*

*livenae*, and other *Pemphigus* species, *Perkinsiella saccharicida*, *Phorodon humuli*, *Psyllidae* such as *Psylla mali*, *Psylla piri* and other *Psylla* species, *Rhopalomyzus ascalonicus*, *Rhopalosiphum maidis*, *Rhopalosiphum padi*, *Rhopalosiphum insertum*, *Sappaphis mala*, *Sappaphis mali*, *Schizaphis graminum*, *Schizoneura lanuginosa*, *Sitobion avenae*, *Trialeurodes vaporariorum*, *Toxoptera aurantiiand*, and *Viteus vitifolii*;

Lepidopterans (Lepidoptera), for example *Agrotis ypsilon*, *Agrotis segetum* and other *Agrotis* species, *Alabama argillacea*, *Anticarsia gemmatalis*, *Argyresthia conjugella*, *Autographa gamma*, *Bupalus piniarius*, *Cacoecia murinana*, *Capua reticulana*, *Chematobia brumata*, *Chilo suppresalis* and other *Chilo* species, *Choristoneura fumiferana*, *Choristoneura occidentalis*, *Cirphis unipuncta*, *Cnaphlocrocis medinalis*, *Cydia pomonella*, *Dendrolimus pini*, *Diaphania nitidalis*, *Diatraea grandiosella*, *Earias insulana*, *Elasmopalpus lignosellus*, *Eupoecilia ambiguella*, *Euxoa* species, *Evetria bouliana*, *Feltia subterranea*, *Galleria mellonella*, *Grapholitha funebrana*, *Grapholitha molesta*, *Heliothis armigera*, *Heliothis virescens*, *Heliothis zea*, *Hellula undalis*, *Hibernia defoliaria*, *Hyphantria cunea*, *Hyponomeuta malinellus*, *Keiferia lycopersicella*, *Lambdina fiscellaria*, *Laphygma exigua*, *Lerodea eufala*, *Leucoptera coffeella*, *Leucoptera scitella*, *Lithocolletis blancardella*, *Lobesia botrana*, *Loxostege sticticalis*, *Lymantria dispar*, *Lymantria monacha*, *Lyonetia clerkella*, *Malacosoma neustria*, *Mamestra brassicae*, *Momphidae*, *Orgyia pseudotsugata*, *Ostrinia nubilalis*, *Panolis flammea*, *Pectinophora gossypiella*, *Peridroma saucia*, *Phalera bucephala*, *Phthorimaea operculella*, *Phyllocnistis citrella*, *Pieris brassicae*, *Plathypena scabra*, *Plutella xylostella*, *Pseudoplusia includens*, *Rhyacionia frustrana*, *Scrobipalpula absoluta*, *Sesamia nonagrioides* and other *Sesamia* species, *Sitotroga cerealella*, *Sparganothis pilleriana*, *Spodoptera frugiperda*, *Spodoptera littoralis*, *Spodoptera litura*, *Thaumatopoea pityocampa*, *Tortrix viridana*, *Trichoplusia ni* and *Zeiraphera canadensis*, orthopterans (Orthoptera), such as *Acrididae*, *Acheta domestica*, *Blatta orientalis*, *Blattella germanica*, *Forficula auricularia*, *Gryllotalpa gryllotalpa*, *Locusta migratoria*, *Melanoplus bivittatus*, *Melanoplus femur-rubrum*, *Melanoplus mexicanus*, *Melanoplus sanguinipes*, *Melanoplus spretus*, *Nomadacris septemfasciata*, *Periplaneta americana*, *Schistocerca americana*, *Schistocerca peregrina*, *Stauronotus maroccanus* and *Tachycines asynamorus*;

termites (Isoptera), such as *Calotermes flavicollis*, *Coptotermes* species, *Dalbulus maidis*, *Leucotermes flavipes*, *Macrotermes gilvus*, *Reticulitermes lucifugus* and *Termes natalensis*;

thrips (Thysanoptera) such as *Frankliniella fusca*, *Frankliniella occidentalis*, *Frankliniella tritici* and other *Frankliniella* species, *Scirtothrips citri*, *Thrips oryzae*, *Thrips palmi*, *Thrips simplex* and *Thrips tabaci*; and Arachnoidea, such as arachnids (Acarina), for example e.g. of the families Argasidae, Ixodidae and Sarcoptidae, such as *Amblyomma americanum*, *Amblyomma variegatum*, *Argas persicus*, *Boophilus annulatus*, *Boophilus decoloratus*, *Boophilus microplus*, *Dermacentor silvarum*, *Hyalomma truncatum*, *Ixodes ricinus*, *Ixodes rubicundus*, *Ornithodorus moubata*, *Otobius megnini*, *Dermanyssus gallinae*, *Psoroptes ovis*, *Rhipicephalus appendiculatus*, *Rhipicephalus evertsi*, *Sarcoptes scabiei*, and *Eriophyidae* species such as *Aculus schlechtendali*, *Phyllocoptrata oleivora* and *Eriophyes sheldoni*; *Tarsonemidae* species such as *Phytonemus pallidus* and *Polyphagotarsonemus latus*; *Tenuipalpidae* species such as *Brevipalpus phoenicis*; *Tetranychidae* species such as *Tetranychus cinnabarinus*, *Tetranychus kanzawai*, *Tetranychus pacificus*, *Tetranychus telarius* and *Tetranychus urticae*, *Panonychus ulmi*, *Panonychus citri*, and *Oligonychus pratensis*.

If the microemulsion according to the invention contain a pyrethroid compound which is active against rice pathogens, the composition may also be used to combat rice phatogens such as rice water weevil (*Lissorhoptrus oryzaphilus*), rice stem borer (*Chilo suppresalis*), rice leaf roller, rice leaf beetle, rice leaf miner (*Agromyca oryzae*), leafhoppers (*Nephotettix* spp.; especially smaller brown leafhopper, green rice leafhopper), planthoppers (Delphacidae; especially white backed planthopper, brown rice planthopper), stinkbugs.

The microemulsions containing of the invention can be applied in conventional manner, usually as an aqueous dilution which is obtained by diluting the microemulsions with water. The required application rate of the pure active compounds without formulation auxiliary depends on the density of the undesired vegetation, on the development stage of the plants, on the climatic conditions of the location where the composition is used and on the application method. In general, the application rate is from 0.001 to 3 kg/ha, preferably from 0.005 to 2 kg/ha and in particular from 0.01 to 1 kg/ha, from 0.1 g/ha to 1 kg/ha, from 1 g/ha to 500 g/ha or from 5 g/ha to 500 g/ha of active substance.

The diluted microemulsions are applied to the plants mainly by spraying, in particular foliar spraying. Application can be carried out by customary spraying techniques using, for example, water as carrier and spray liquor rates of from about 100 to 1000 l/ha (for example from 300 to 400 l/ha).

Moreover, it may be useful to apply the microemulsions according to the invention jointly as a mixture with other crop protection products, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

In a further embodiment of the invention, the microemulsions contain a pyrethroid compound which is active against non-crop pests. Therefore the invention also relates to a method for controlling non-crop pests comprising contacting the pests or their food supply, habitat, breeding grounds or their locus with formulation according to the invention comprising at least an insecticide.

The invention further relates to the use of a microemulsion according to the invention for the protection of non-living organic materials against non-crop pests.

Non-crop pests are pests of the classes Chilopoda and Diplopoda and of the orders Isoptera, Diptera, Blattaria (Blattodea), Dermaptera, Hemiptera, Hymenoptera, Orthoptera, Siphonaptera, Thysanura, Phthiraptera, Araneida, Parasitiformes and Acaridida, for example:

centipedes (Chilopoda), e.g. *Scutigera coleoptrata*, millipedes (Diplopoda), e.g. *Narceus* spp., spiders (Araneida), e.g. *Latrodectus mactans*, and *Loxosceles reclusa*, scabies (Acaridida): e.g. *sarcoptes* sp, ticks and parasitic mites (Parasitiformes): ticks (Ixodida), e.g. *Ixodes scapularis*, *Ixodes holocyclus*, *Ixodes pacificus*, *Rhiphicephalus sanguineus*, *Dermacentor andersoni*, *Dermacentor variabilis*, *Amblyomma americanum*, *Ambryomma maculatum*, *Ornithodorus hermsi*, *Ornithodorus turicata* and parasitic mites (Mesostigmata), e.g. *Ornithonyssus bacoti* and *Dermanyssus gallinae*, termites (Isoptera), e.g. *Calotermes flavicollis, Leucotermes flavipes, Heterotermes aureus, Reticulitermes flavipes, Reticulitermes virginicus, Reticulitermes lucifugus, Termes natalensis,* and *Coptotermes formosanus,* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,*

Earwigs (Dermaptera), e.g. *forficula auricularia,* true bugs (Hemiptera), e.g. *Cimex lectularius, Cimex hemipterus, Reduvius senilis, Triatoma* spp., *Rhodnius prolixus,* and *Arilus critatus,* ants, bees, wasps, sawflies (Hymenoptera), e.g. *Crematogaster* spp., *Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Dasymutilla occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile,* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina,* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

The present invention also relates to a method for the protection of non-living organic materials against non-crop pests as mentioned above comprising contacting the pests or their food supply, habitat, breeding grounds, their locus or the non-living organic materials themselves with a pesticidally effective amount of a formulation according to the invention.

Furthermore, a formulation according to the invention can be used for protecting cellulose-containing non-living organic materials, e.g. for protecting cellulose-containing non-living organic materials against non-crop pests from the Isoptera, Diptera, Blattaria (Blattodea), Hymenoptera, and Orthoptera orders, most preferably the Isoptera orders.

The present invention also provides a method for protecting cellulose-containing non-living organic materials against non-crop pests, preferably from the Isoptera, Diptera, Blattaria (Blattodea), Hymenoptera, and Orthoptera orders, most preferably the Isoptera orders, comprising contacting the pests or their food supply, habitat, breeding grounds, their locus or the cellulose-containing non-living organic materials themselves with a formulation according to the invention comprising at least an insecticide.

Furthermore, a composition according to the invention comprising at least one pyrethroid can be used for used for protection of animals against non-crop pest of the class Chilopoda, and of the orders Araneida, Hemiptera, Diptera, Phthiraptera, Siphonaptera, Parasitiformes and Acaridida by treatment of the pests in water bodies and/or in and around buildings, including but not limited to walls, ground, manure piles, turf grass, pastures, sewers and materials used in the construction of buildings and also mosquito nets, mattresses and bedding, with a formulation according to the present invention.

Animals include warm-blooded animals, including humans and fish. Thus, a formulation according to the invention comprising at least an insecticide can be used for protection of warm-blooded animals such as cattle, sheep, swine, camels, deer, horses, poultry, rabbits, goats, dogs and cats.

Furthermore, a formulation according to the invention can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). A formulation according to the invention comprising at least an insecticide can be are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant control composition of the present invention is directly applied to the nest of the ants or to its surrounding or via bait contact.

Furthermore, a microemulsion according to the invention can be applied preventively to places at which occurrence of the pests is expected.

In a further aspect, the invention relates to the treatment of seeds. The term seed treatment comprises all suitable seed treatment techniques known in the art, such as, but not limited to, seed dressing, seed coating, seed soaking, seed film coating, seed multilayer coating, seed encrusting, seed dripping, and seed pelleting. The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

If the microemulsion according to the present invention is intended for seed treatment purposes, the formulation may optionally comprise also dyes or pigments. Suitable pigments or dyes for seed treatment formulations are pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The invention furthermore comprises seeds treated with the microemulsion according to the present invention.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugar beet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, microemulsion may also be used for the treatment seeds from plants, which tolerate the action of herbicides or fungicides or insecticides or nematicides owing to breeding, mutation and/or genetic engineering methods.

For example, microemulsion can be employed can be employed in transgenic crops which are resistant to herbicides from the group consisting of the sulfonylureas (EP-A-0257993, U.S. Pat. No. 5,013,659), imidazolinones (see for example U.S. Pat. No. 6,222,100, WO 0182685, WO 0026390, WO 9741218, WO 9802526, WO 9802527, WO 04/106529, WO 05/20673, WO 03/14357, WO 03/13225, WO 03/14356, WO 04/16073), glufosinate-type (see for example EP-A-0242236, EP-A-242246) or glyphosate-type (see for example WO 92/00377) or in plants resistant towards herbicides selected from the group of cyclohexadienone/Aryloxyphenoxypropionic acid herbicides (U.S. Pat. No. 5,162, 602, U.S. Pat. No. 5,290,696, U.S. Pat. No. 5,498,544, U.S. Pat. No. 5,428,001, U.S. Pat. No. 6,069,298, U.S. Pat. No. 6,268,550, U.S. Pat. No. 6,146,867, U.S. Pat. No. 6,222,099, U.S. Pat. No. 6,414,222) or in transgenic crop plants, for example cotton, with the capability of producing *Bacillus thuringiensis* toxins (Bt toxins) which make the plants resistant to certain pests (EP-A-0142924, EP-A-0193259).

Furthermore, microemulsion can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application is carried out by spraying or dusting the seeds with an effective amount of the microemulsion before sowing of the plants and before emergence of the plants.

In the treatment of seeds the corresponding microemulsions are applied by treating the seeds with an effective amount of the microemulsion. Herein, the application rates of the pyrethroid compound P are generally from 0.1 g to 10 kg per 100 kg of seed, preferably from 1 g to 5 kg per 100 kg of seed, in particular from 1 g to 2.5 kg per 100 kg of seed. For specific crops such as lettuce and onions the rates can be higher.

The following examples shall further illustrate the present invention. The scope of this invention should not be deemed limited by the examples, but encompasses the entire subject matter defined in the claims. In the examples, all percentage is percent by weight of the total composition.

I Analytics:
Particle sizes were determined by dynamic light scattering with a Zetasizer Nano ZS, Malvern Instruments, at 25° C.

II. Preparation of the Compositions of the Invention:

Examples 1 to 4, Comparative Examples 1 and 2

The entire ingredients as given in table 1 were added into a vessel equipped with a stirrer and the mixture was stirred at 55° C. for 1 hour. Then the mixture was cooled down at ambient temperature. The thus obtained liquid mixtures were clear and uniform.

TABLE 1

| Ingredients | Ex. 1 | Ex. 2 | Ex. 3 | Ex. 4 | Comp. Ex. 1 | Comp. Ex. 2 |
|---|---|---|---|---|---|---|
| flucythrinate [1] | 4.4% | 4.4% | 4.4% | — | 4.4% | 4.4% |
| alpha-cypermethrin | — | — | — | 1.0% | — | — |
| surfactant 1 [2] | 12.0% | 12.0% | 12.0% | 12.0% | 8.0% | 12.0% |
| surfactant 2 [3] | 4.0% | 4.0% | 4.0% | 4.0% | 2.0% | 4.0% |
| 3-methoxy-3-methyl butyl acetate | 7.5% | — | — | — | — | — |
| propylene glycol mono methyl ether acetate | — | 7.5% | — | 20.0% | — | — |
| propylene glycol mono ethyl ether acetate | — | — | 7.5% | — | — | — |
| ethylene glycol | — | — | — | — | 5.0% | — |
| diethylene glyol monomethylether | — | — | — | — | — | 7.5% |
| D.I. water | 72.1% | 72.1% | 72.1% | 63.0% | 80.6% | 72.1% |

[1] (R,S)-α-cyano-3-phenoxybenzyl (S)-2-difluoromethoxyphenyl)-3-methylbutyrate)

[2] A formulation containing 37% by weight of polyoxyethylene tristyryl phenyl ether (19 mol ethylene oxide), 12% by weight of polyoxyethylene distyryl phenyl ether-formaldehyde condensate (26 mol ethylene oxide), 31% by weight of sodium alkyl benzene sulfonate and 20% of water.

[3] polyoxyethylene styryl phenyl ether (14 mol ethylene oxide)

19

III. Stability Tests

1. Crystallization of Active Ingredient

SS-isomer of flucythrinate was milled in a mortar. 10 mg of the thus obtained powder were added to 100 ml of the microemulsions of examples 1 to 3 and to the comparison sample. After storing the samples at 5° C. for 3 weeks, the growth of crystal seed in each sample was evaluated by microscopic observation. *SS-isomer of flucythrinate (Solid; at less than ca. 52° C.)

The comparison samples Comp. Ex 1 and 2, not including ester solvent, showed crystal growth of flucythrinate crystals, while no crystal growth was observed in the microemulsions of the examples 1 to 3.

2. Dilution Stability

In order to confirm the stability after dilution with water, the droplet size distribution after dilution of the microemulsion was measured by light scattering. The assay was done soon after dilution and after 24 hours, and the dilution rate was 1:30 (w/w). The results are presented in Table 2.

TABLE 2

| | Average droplet size (Z-average size) | | | | |
|---|---|---|---|---|---|
| | Ex. 1 | Ex. 2 | Ex. 3 | Ex. 4 | Comp. Ex. 1 |
| Soon after dilution | 7.5 nm | 7.5 nm | 7.5 nm | 4.2 | 12.4 nm |
| 24 hours after dilution | 7.5 nm | 7.4 nm | 7.5 nm | 4.4 | 21.0 nm |

The microemulsion of the comparative example showed an intense increase of droplet size distribution after dilution with water, while in the microemulsions of the examples 1 to 4 no shift of droplet size distribution was observed. This means that the dilution stability of the microemulsions of the examples 1 to 4 is much better than the dilution stability of the comparative example.

3. Freezing Point

The freezing point of the microemulsions was measured. The results are shown in Table 3.

TABLE 3

| Freezing point (° C.) | | | |
|---|---|---|---|
| Ex. 1 | Ex. 2 | Ex. 3 | Comp. Ex. 1 |
| −7° C. | −12° C. | −12° C. | −7° C. |

These results indicate that solvents I in the examples 1 to 3 play a role as the anti-freezing agent like ethylene glycol in comparative example.

We claim:

1. A pesticidal aqueous microemulsion formulation, consisting of:
a) from 0.1 to 8% by weight of at least one organic pyrethroid compound P;
b) from 1 to 25% by weight of at least one organic solvent, selected from compounds of the formula I

wherein
m is 1, 2 or 3,
$R^1$ is $C_1$-$C_6$-alkyl or $C(O)R^3$,
$R^2$ is $C_1$-$C_4$-alkyl,
Alk is straight chain or branched $C_2$-$C_6$-alkylene, and
$R^3$ is $C_1$-$C_4$-alkyl;

20 c) from 1 to 30% by weight of a surfactant mixture, comprising:
i) at least one anionic surfactant selected from the group consisting of $C_8$-$C_{22}$-alkyl sulfates, $C_1$-$C1_6$-alkyl naphthalene sulfonates and $C_1$-$C1_6$-alkyl benzene sulfonates; and
ii) at least one non-ionic surfactant selected from the group consisting of polyoxy-$C_2$-$C_3$-alkylene $C_8$-$C_{22}$-alkyl ethers, polyoxy-$C_2$-$C_3$-alkylene $C_8$-$C_{22}$-alkyl-benzene ethers, polyoxy-$C_2$-$C_3$-alkylene mono-, di- or tristyryl phenyl ethers and polyoxy-$C_2$-$C_3$-alkylene mono- or distyryl phenyl ether-formaldehyde condensates and acetylene glycols; and
d) water;
wherein the total of the amounts of the at least one compound P, the at least one solvent, the surfactant mixture, and water is 100% by weight, wherein the total amount of organic solvent of formula I is from 1 to 25% by weight, wherein the pesticidal aqueous microemulsion formulation comprises at least 50% by weight of water and wherein the weight ratio of anionic surfactant to non-ionic surfactant is from 0.1:1 to 10:1.

2. The formulation according to claim 1, wherein the solvent is selected from the group consisting of 3-methoxy-3-methyl butyl acetate, propylene glycol mono methyl ether acetate, propylene glycol mono ethyl ether acetate, dipropylene glycol methyl ether acetate, propylene glycol diacetate, ethylene glycol mono butyl ether acetate, diethylene glycol mono butyl ether acetate and mixtures thereof.

3. The formulation according to claim 1, wherein Alk in formula I is straight chain or branched $C_3$-$C_6$-alkylene.

4. The formulation according to claim 1, wherein the surfactant is a mixture consisting of:
i) at least one anionic surfactant selected from $C_1$-$C1_6$-alkyl benzene sulfonates, and
ii) at least one non-ionic surfactant selected from the group consisting of polyoxy-$C_2$-$C_3$-alkylene mono-, di- or tristyryl phenyl ethers and polyoxy-$C_2$-$C_3$-alkylene mono- or distyryl phenyl ether-formaldehyde condensates.

5. The formulation according to claim 1, wherein the weight ratio of the organic solvent of formula I to the pesticide compound P is from 0.5:1 to 100:1.

6. The formulation according to claim 1, wherein the weight ratio of the surfactant to the total amount of the solvent of formula I plus pesticide compound P is from 0.1:1 to 10:1.

7. The formulation according to claim 1, wherein the at least one compound P is selected from the group consisting of alpha cypermethrin and flucythrinate.

8. A method of combating harmful organisms comprising contacting said harmful organisms, their habit, breeding ground, food supply, plant, seed, soil, area, material or environment in which the harmful organisms are growing or may grow, or the materials, plants, seeds, soils, surfaces or spaces to be protected from attack or infestation by harmful organisms with an effective amount of a formulation as claimed in claim 1.

9. A method for protecting crops from attack or infestation by harmful organisms comprising contacting a crop with an effective amount of a formulation as claimed in claim 1.

10. A method for protecting seeds from attack or infestation by harmful organisms comprising contacting a seed with an effective amount of a formulation as claimed in claim 1.

11. The composition of claim 1, wherein, the pesticidal aqueous microemulsion formulation forms an emulsion having dispersed particles, the particles having an average particle diameter of at most 200 nm.

12. The composition of claim 1, wherein the pesticidal aqueous microemulsion formulation comprises at least 60% by weight of water.

13. The composition of claim 1, wherein the weight ratio of anionic surfactant to non-ionic surfactant is from 2:1 to 5:1.

* * * * *